(12) United States Patent
Sakai et al.

(10) Patent No.: US 6,498,164 B1
(45) Date of Patent: Dec. 24, 2002

(54) BARBITURIC ACID DERIVATIVE AND PREVENTIVE AND THERAPEUTIC AGENT FOR BONE AND CARTILAGE CONTAINING THE SAME

(75) Inventors: Kunikazu Sakai, Tokyo (JP); Yusuke Satoh, Saitama (JP)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/647,280

(22) PCT Filed: Mar. 23, 1999

(86) PCT No.: PCT/IB99/00961

§ 371 (c)(1),
(2), (4) Date: Oct. 19, 2000

(87) PCT Pub. No.: WO99/50252

PCT Pub. Date: Oct. 7, 1999

(30) Foreign Application Priority Data

Mar. 27, 1998 (JP) ............................................. 10-100355

(51) Int. Cl.[7] .............................................. A61K 31/515
(52) U.S. Cl. ........................ 514/270; 544/300; 544/301; 544/302
(58) Field of Search ................................ 544/300, 301, 544/302; 514/270

(56) References Cited

U.S. PATENT DOCUMENTS 2,921,072 A * 1/1960 Ferguson .................. 260/256.4
3,828,043 A * 8/1974 Kay et al. ................... 260/257
5,102,760 A * 4/1992 Yokoya et al. ................ 430/78

* cited by examiner

Primary Examiner—John M. Ford
(74) Attorney, Agent, or Firm—Bierman, Muserlian and Lucas

(57) ABSTRACT

A compound of the formula

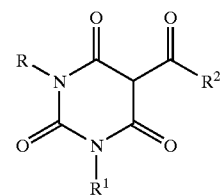

wherein the substituents are as defined in the specification and solvates and salts thereof useful for treating bone and cartilage diseases.

5 Claims, No Drawings

BARBITURIC ACID DERIVATIVE AND PREVENTIVE AND THERAPEUTIC AGENT FOR BONE AND CARTILAGE CONTAINING THE SAME

This application is a 371 of PCT/IB/00961, filed Mar. 23, 1999.

The present invention relates to a novel barbituric acid derivative and the method of the prevention and treatment by using the same of malignant hypercalcemia, osteolytic diseases such as Paget's disease of bone and osteoporosis, such diseases with the denaturation and necrosis of a cartilage as osteoarthritis, necrosis of head of femur, and articular rheumatism occurring in a knee, shoulder, and joint.

Japan has been gradually shifting to an aging society and, therefore, bone resorption diseases such as osteoporosis are becoming a big social problem. The bone resorption diseases are diseases of bone caused by abnormal sthenia of bone resorption exemplified by malignant hypercalcemia caused by myeloma and lymphoma, bone Paget's disease by local bone resorption, and osteoporosis caused by many factors such as aging and menopause. Although, at present, a female hormone, calcitonin, activated vitamin D3, parathyroid hormone, bisphosphonate, and ipriflavone, etc. are being used for therapeutic treatment, these agents have some defects respectively so as to remain as a symptomatic therapy.

On the other hand, osteoarthritis, necrosis of head of femur, and joint rheumatism are a disease occurring a defect of cartilage and bone caused by denaturation and necrosis of joint cartilage and subcartilaginous bone by various factors such as mechanical stresses, senescence, inflammation. The defect of bone largely affects the lowering of the quality of life through the deformation and pain of a joint. Any agents have not substantially existed to inhibit or repair effectively the defect of cartilage for the diseases.

Barbituric acid derivatives are a group of compounds which are used for medicinal drugs, agricultural chemicals, and many other purposes, and many derivatives are known. For example, there are an anticancer drug (refer to WO9116315), photosensitive materials for electronic photography (refer to Japanese Patent Application Laid-open Nos. 179361/91 and 111852/91), a vermifuge (refer to EP 192180), insecticides (EP 455300, DE 3903404, and GB 1339748), herbicides (U.S. Pat. No. 4,797,147 and Japanese Patent Application laid-open No. 154275/75), and a bactericide (EP 517660).

The present inventors first elucidated the structure and the strong inhibiting action of bone resorption, which had not been previously known as far as the inventors' knowledge is concerned, of a series of compounds related to the present invention.

The inventors of the present invention formerly found substances showing a strong inhibiting action of bone resorption among derivatives of polyhydroxyphenol (Japanese Patent Application No. 137991/97). As a result of further research and an analysis of structure-activity relationship of those compounds, the inventors found a strong activity of a novel barbituric acid derivative and finally completed the present invention.

Thus, the purpose of the present invention is to provide a novel and useful barbituric acid derivative, the salt thereof and the solvate thereof, and a method of prevention and treatment of various diseases affecting bones and cartilages by using these compounds.

The subject of the invention is a barbituric acid derivative represented by the following general formula (I), the salt thereof or the solvate thereof:

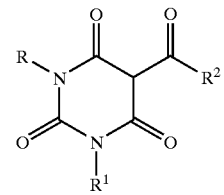

(wherein each of R or $R^1$ independently represents a hydrogen atom, a substituted or an unsubstituted alkyl group or an alkenyl group of $C_1$–$C_{15}$, a substituted or an unsubstituted arylmethyl group, or a substituted or an unsubstituted aryl group, and $R^2$ represents a substituted or an unsubstituted alkyl group or an alkenyl group of $C_1$–$C_{15}$, a substituted or.

The present invention relates to a barbituric acid derivative shown in said general formula (I), the salt thereof or the solvates thereof containing one or more compounds, and a composition of a medicinal drug containing a carrier that is acceptable for drug manufacturing, preferably, a composition of a medicinal drug being a preventive and therapeutic agent for diseases affecting bones and cartilages.

Further, the present invention relates to a use of a barbituric acid derivative shown in said general formula (I), the salt thereof or the solvate thereof containing one or more compounds for manufacturing a composition of a medicinal drug for prevention and therapy of diseases affecting bones and cartilages.

Furthermore, the present invention relates to a method for prevention and therapy of diseases affecting bones and cartilages by administration of an effective amount of a barbituric acid derivative shown in said general formula (I), the salt thereof or the solvate thereof containing one or more compounds for prevention and therapy of diseases affecting bones and cartilages.

In the compound shown in said general formula (I) of the present invention, alkyl groups are straight-chain or branched alkyl groups of 1–15 carbon atoms, preferably 2–10, more preferably 4–10, and alkenyl groups are straight-chain or branched unsaturated hydrocarbon groups of 2–15 carbon atoms, preferably 3–10, more preferably 4–10; preferably, unsaturated hydrocarbon groups of one or more carbon—carbon double bonds.

In the compound shown in said general formula (I) of the present invention, aryl groups are monocyclic, polycyclic, or condensed ring aryl groups of 6–30 carbon atoms, preferably 6–20, more preferably 6–10; aryl groups of the present invention are monocyclic, polycyclic, or condensed ring heterocyclic aromatic groups of at least one or more nitrogen atoms, oxygen atoms, or sulfur atoms in an aromatic ring, of which size of one ring is 5–20 members, preferably 5–10 members, more preferably 5–7 members, and may be condensed with a ring consisted of saturated or unsaturated hydrocarbon groups.

In the compound shown in said general formula (I) of the present invention, arylmethyl groups are exemplified by methyl groups made by substitution of said aryl group.

In said general formula (I) of the present invention, alkyl groups, alkenyl groups, arylmethyl groups, or aryl groups may be substituted by a substitution group that does not inhibit activities in medical purposes of the present invention.

The compound shown in said general formula (I) of the present invention might be protected by a protecting group allowing production of an active body in a living body to express a physiological activity in the living body.

Substitution groups of said alkyl groups, alkenyl groups, arylmethyl groups, or aryl groups in said general formula (I) of the present invention can be one made by substitution of these groups each other, when mutual substitution of these groups is possible. Examples are aryl groups substituted by an alkyl group, arylmethyl groups substituted by an alkyl group, alkyl groups substituted by an aryl group, and alkenyl groups substituted by an aryl group.

Other substitution groups are exemplified by a hydroxyl group, an amino group, an alkoxy group having said alkyl groups, an alkylthio group, a mono- or a dialkylamino group, halogen atoms such as chlorine, bromine, and fluorine, alkylenedioxy groups such as a methylenedioxy group and a 2,2-dimethylmethylenedioxy group, a cyano group, and a nitro group.

Preferable substitution groups are exemplified by lower alkyl groups such as a methyl group, an ethyl group, an n-propyl group, an isopropyl group, an n-butyl group, and a t-butyl group, aryl groups such as a phenyl group and a naphthyl group, lower alkoxy groups such as a methoxy group, an ethoxy group, and an n-propoxy group, di- lower alkylamino groups such as a dimethylamino group, a diethylamino group, and a dipropylamino group, halogen atoms such as iodine, bromine, chlorine, and fluorine, alkylenedioxy groups such as a methylenedioxy group, a 2,2-dimethylmethylenedioxy group, a hydroxyl group, an amino group, a cyano group, and a nitro group, etc.

Aryl groups in the compounds shown in said general formula (I) of the present invention are exemplified by a phenyl group, a naphthyl group, an anthracenyl group, a pyridyl group, a quinolyl group, a thienyl group, and a pyrrolyl group.

Substitution groups of a substituted alkyl group or a substituted alkenyl group are preferably specified by an atomic group introduced in replacement to a hydrogen atom in preparing a derivative by substitution of a hydrogen atom of these groups to another atom group. The substitution groups can be a hydroxyl group, an alkoxy group, iodine, bromine, chlorine, and fluorine, an amino group, a cyano group, and a nitro group. Substitution groups of a substituted arylmethyl group are preferably atomic groups introduced in replacement to a hydrogen atom, when a derivative is prepared by substituting another atomic group of a residue formed by removing a single hydrogen atom of the benzene ring of an aromatic compound to a hydrogen atom of a compound of which hydrogen atom has been substituted by a methyl group. These substitution groups are exemplified by a hydroxyl group, an alkoxy group, iodine, bromine, chlorine, fluorine, an amino group, a cyano group, and a nitro group. Substitution groups for substituting an aryl group are preferably exemplified by those in which a residue group prepared by removing a single hydrogen atom from the benzene ring of an aromatic compound has been substituted by a hydroxyl group, an alkoxy group, iodine, bromine, chlorine, fluorine, an amino group, a cyano group, and a nitro group, etc.

Alkyl groups substituted or unsubstituted shown in said general formula (I) of the substitution groups R and $R^1$ of a barbituric acid derivative are preferably exemplified by a methyl, an ethyl, a propyl, a butyl, a pentyl, a hexyl, a heptyl, an octyl, a nonyl, a decanyl, an undecanyl, a dodecyl, a tridecyl, a tetradecyl, or a pentadecyl group, etc.; in addition to their isomers, those substituted or unsubstituted to these groups by said substitution group are preferable.

Alkenyl groups substituted or unsubstituted—shown in said general formula (I) of the substitution groups R and $R^1$ of a barbituric acid derivative are preferably exemplified by an ethenyl, a propenyl, a butenyl, a pentenyl, a hexenyl, a heptentyl, an octenyl, a nonenyl, a decenyl, an undecenyl, a dodecenyl, a tridecenyl, a tetradecenyl, or a pentadecenyl group, etc.; in addition to their isomers, those substituted or unsubstituted to these groups by said substitution group are preferable.

Arylmethyl groups substituted or unnsubstituted shown in said general formula (I) of the substitution groups R and $R^1$ of a barbituric acid derivative are preferably exemplified by a phenylmethyl, a naphthylmethyl, an anthracenylmethyl, a pyridylmethyl, a quinolylmethyl, a thienylmethyl, or a pyrrolylmethyl group, etc.; in addition, those substituted to these groups by said substitution groups and preferably exemplified by those substituted or unsubstituted to these groups by said substitution groups such as a hydroxyl group, an alkoxy group, iodine, bromine, chlorine, fluorine, an amino group, a cyano group, or a nitro group, etc.

Alkyl groups substituted or unsubstituted shown in said general formula (I) of the substitution groups $R^2$ of a barbituric acid derivative are preferably exemplified by a methyl, an ethyl, a propyl, a butyl, a pentyl, a hexyl, a heptyl, an octyl, a nonyl, a decanyl, an undecanyl, a dodecyl, a tridecyl, a tetradecyl, or a pentadecyl group, etc.; in addition to their isomers, those substituted or unsubstituted to these groups by said substitution group are preferable.

Alkenyl groups substituted or unsubstituted shown in said general formula (I) of the substitution groups $R^2$ of a barbituric acid derivative are preferably exemplified by an ethenyl, a propenyl, a butenyl, a pentenyl, a hexenyl, a heptentyl, an octenyl, a nonenyl, a decenyl, an undecenyl, a dodecenyl, a tridecenyl, a tetradecenyl, or a pentadecenyl group, etc.; in addition to their isomers, those substituted or unsubstituted to these groups by said substitution group are preferable.

Arylmethyl groups substituted or unsubstituted shown in said general formula (I) of the substitution groups $R^2$ of a barbituric acid derivative are preferably exemplified by a phenylmethyl, a naphthylmethyl, an anthracenylmethyl, a pyridylmethyl, a quinolylmethyl, a thienylmethyl, or a pyrrolylmethyl group, etc.; in addition, those substituted to these groups by said substitution groups and preferably exemplified by those substituted or unsubstituted to these groups by said substitution groups such as a hydroxyl group, an alkoxy group, iodine, bromine, chlorine, fluorine, an amino group, a cyano group, or a nitro group, etc.

Aryl groups substituted or unsubstituted shown in said general formula (I) of the substitution groups $R^2$ of a barbituric acid derivative are preferably exemplified by a phenyl, a naphthyl, an anthracenyl, a pyridyl, a quinolyl, a thienyl group, or a pyrrolyl group, etc.; in addition, those substituted or unsubstituted to these groups by said substitution groups are preferable.

Preferable compounds of the compound shown in said general formula (I) of the present invention are specifically exemplified as follows:

1,3-dibenzyl-5-(3-methyl-1-oxobutyl)barbituric acid (Compound No. 1),
1,3-dibenzyl-5-(phenylacetyl)barbituric acid (Compound No. 2),
1,3-dibenzyl-5-(2-thienylacetyl)barbituric acid (Compound No. 3),
1,3-bis(3-methylbutyl)-5-(3-methyl-1-oxobutyl)barbituric acid (Compound No. 4),
1-benzyl-3-(3-methylbutyl)-5-(3-methyl-1-oxobutyl) barbituric acid,
1-benzyl-3-(3-methylbutyl)-5-(phenylacetyl)barbituric acid, 1-benzyl-3-(3-methylbutyl)-5-(2-thienylacetyl)barbituric acid,
1,3-bis(3-methyl-2-butenyl)-5-(3-methyl-1-oxobutyl)barbituric acid,
1,3-bis(3-methyl-2-butenyl)-5-(phenylacetyl)barbituric acid,
1,3-bis(3-methyl-2-butenyl)-5-(2-thienylacetyl)barbituric acid,
1-benzyl-3-(3-methyl-2-butenyl)-5-(3-methyl-1-oxobutyl)barbituric acid,
1-benzyl-3-(3-methyl-2-butenyl)-5-(phenylacetyl)barbituric acid,
1-benzyl-3-(3-methyl-2-butenyl)-5-(2-thienylacetyl)barbituric acid,
1-(3-methyl-2-butenyl)-3-(3-methylbutyl)-5-(3-methyl-1-oxobutyl)barbituric acid,
1-(3-methyl-2-butenyl)-3-(3-methylbutyl)-5-(phenylacetyl)barbituric acid,
1-(3-methyl-2-butenyl)-3-(3-methylbutyl)-5-(2-thienylacetyl) barbituric acid.

The compound shown in said general formula (I) of the present invention can be synthesized by a conventional method for synthesis. For example, in a reaction formula represented by the following formula, synthesis can be made easily by a condensation reaction of a barbituric acid derivative represented by the following formula (II) and an acylation agent represented by the following formula (III) (refer to the following formula):

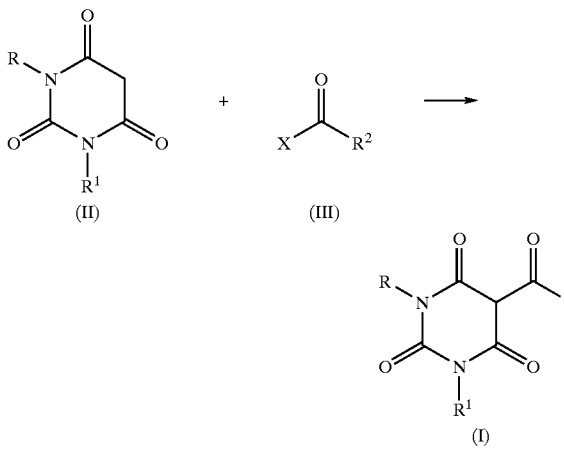

Acylation agents used are exemplified by acyl halides, acid anhydrides, or carboxylic acids, etc. It is well known by a person skilled in the art that condensation agents used for these reactions are individually selected according to a reaction applied. When an acylation agent (III) is acyl halides or acid anhydrides, a base lacking nucleophilic reaction, preferably a tertiary amine is used as a condensation agent. Examples are aromatic amines such as pyridine and quinoline, etc., tertiary amines such as triethylamine, diisopropylethylamine, and N-methylpyrrolidine, etc., and aralkyl amines such as N,N-dimethyl aniline, etc. A solvent is used for the reaction, however, it can be used that is not restrictive, but applicable for aniline, etc. A solvent is used for the reaction; however, it can be used that is not restrictive, but applicable for those inactive to both acylation agent and tertiary amine. Pyridine, and triethylamine, etc. are sometimes used for a condensation agent in combination of a solvent (refer to J. Org. Chem. 45: 4606, 1980; EP 455300; Japanese Patent Application laid-open No. 102358/91; Japanese Patent Application laid-open No. 111852/91).

When an acylation agent (III) is a free carboxylic acid, oxyphosphorus chloride is used, for example, as a condensation agent (refer to GB 1339748).

There are some methods for preparation of a barbituric acid derivative (II) to acylated in said reaction formula. Those methods are easily contrived by a person skilled in the art. For example, the manufacture can be conducted by the formula presented below (refer to the following formula).

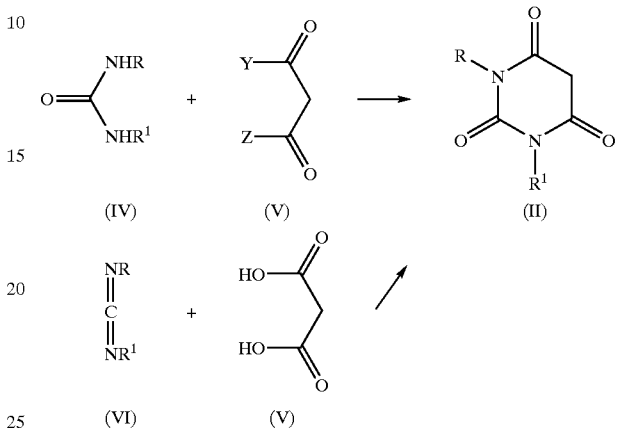

Examples are a method by condensation of an urea derivative (IV) and a malonic acid derivative (V) (Y and Z are halogen atoms such as chlorine or bromine, etc., or a hydroxyl group, or form an ester group together with a carbonyl group), and a method by condensation of a carbodiimide derivative (VI) and malonic acid (V') (refer to EP 455300).

The urea derivative (IV) and a carbodiimide derivative (VI), etc. are compounds generally known as materials, and their preparation has been described in the following reference in detail (Reference: S. R. Sandler and W. Karo, Chapter 6/Ureas, Chapter 9/Carbodiimides, Academic Press, 1986).

The bone resorption inhibiting activity of the barbituric acid derivative prepared according to an aforementioned method was tested by the pit formation assay method. As a result, the compound of the present invention showed an excellent inhibiting ratio to bone resorption in the concentration of $1\times10^{-5}$ M.

Therefore, these compounds have a strong inhibiting activity to bone resorption. A barbituric acid derivative, the salt thereof, or the solvates thereof shown by the general formula (I) of the present invention is useful as an effective ingredient of medicinal drug for prevention and therapeutic treatment of bone and cartilage diseases. The present invention provides a composition of a medicinal drug containing one or more compounds as an effective ingredient, a method by using the composition for prevention and therapeutic treatment of various diseases related to the inhibiting action of bone resorption, and a use of these compounds for preparation of the composition of a medicinal drug.

The present invention relates to a composition of a medicinal drug containing one or more compounds shown in said general formula (I), the salt thereof or the solvate thereof, or a substance protected thereby (for example, a prodrug to become an active drug in a living body), that are acceptable for drug manufacturing, as an effective ingredient. The composition of a medicinal drug of the present invention relates to a composition of a medicinal drug containing various carriers that is acceptable for drug manufacturing. The composition of a medicinal drug of the present invention has an activity of inhibiting bone resorption and is useful as a preventive or therapeutic agent for diseases affecting bones and cartilages.

The diseases affecting bones and cartilages of the present invention include bone resorption diseases such as malignant hypercalcemia, bone Paget's disease, and osteoporosis and diseases accompanying with denaturation and necrosis of cartilage such as osteoarthritis, necrosis of head of femur, and joint rheumatism occurring in knee, shoulder, and hip joint.

A clinical administration dose as the effective ingredient of the present invention ranges in general 0.01 g–2 g a day (ca. 0.15 mg–30 mg/kg/day) for an adult person as the compound of the present invention, preferably 0.1–2 g a day (ca. 1.5 mg–30 mg/kg/day) for an adult person, and more preferably 0.1–1 g a day (ca. 1.5 mg–15 mg/kg/day) for an adult person, which are changeable according to a method of administration, a stage of the disease, and a condition of a patient.

A possible administration method for the composition of a medicinal drug of the present invention includes intravenous, intramuscular, oral, and intrarectal administrations, in the intravenous administration, an intravenous drip can be applied in addition to a conventional intravenous injection.

A drug manufacturing method for the composition of a medicinal drug containing the compound of the present invention is exemplified by a conventional method by using a conventional excipient and a conventional additive.

An injection preparation can be, for example, a powder preparation for injection. In this case, a medicinal drug is prepared by adding one or more appropriate water soluble excipients such as mannitol, sucrose, lactose, maltose, glucose, fructose, etc. to water to dissolve, dividing into a vial or an ampoule followed by freeze drying and hermetic packing for final preparation. In preparation for an oral administration, an enteric coated agent can be prepared in addition to a conventional tablet, a capsule, a granule, a fine granule, and a powder.

In preparing the enteric coated agent, a tablet, a granule, or a fine granule can be prepared by adding, additives such as a lubricant such as mannitol, sucrose, lactose, maltose, starch, silica anhydride, calcium phosphate, etc., a binder such as carboxymethylcellulose, methylcellulose, gelatin, gum arabic, etc., and a disintegrant such as calcium carboxymethylcellulose, followed by coating with one or more enteric base agents such as cellulose, acetate phthalate, hydroxypropylmethylcellulose phthalate, hydroxypropylmethylcellulose acetyl succinate, polyvinyl alcohol phthalate, styrene, a copolymer of maleic acid anhydride, methylacrylate, and a copolymer of methylacrylate and, if necessary, adding a colorant such as titanium oxide to make a preparation. A capsule preparation can be made by filling enteric granules or fine granules prepared thereby in a capsule. On the other hand, it is possible that a capsule prepared by a conventional method is coated with said enteric base agent to make enteric and made to an enteric capsule by using a capsule prepared by using said enteric base agent singly or by mixing gelatin therewith.

For a suppository, it can be prepared by adding a semi-synthesized base agent which is dissolved after preparation by mixing a monoglyceride of fatty acid and a diglyceride of fatty acid in various proportions to cacao butter or triglyceride of fatty acid, followed by kneading mildly and pour into a mold to form a suppository.

The present invention will now be described in detail with reference to the following referencial examples, examples, and a test example that by no means limit the scope of the invention.

REFERENTIAL EXAMPLE 1

Preparation of N,N'-Dibenzylurea

Heated was a mixture of urea 5.84 g (9.72 mmol) and benzylamine 25.0 g (23.3 mmol, 2.4 equivalents) at 150° C.–155° C. for 5 hours attaching with an air cooler. During the heating, observed was the ammonia gas evolution from colorless liquid reaction mixture. By cooling, it turned solidified at around room temperature. Purified was the reaction product by recrystallization from ethanol-benzene (1:1 mixture) to give N,N'-dibenzylurea 14.0 g as white fine needles (59.9% yield).

NMR (DMSO-CDCl$_3$) δ4.33 (2H, d, J=5.8 Hz), 6.02 (1H, bt), 7.19–7.32 (5H, m).

REFERENTIAL EXAMPLE 2

Preparation of N,N'-Bis(3-methylbutyl)urea

Heated was a mixture of urea 0.601 g (10.0 mmol) and 3-methylbutylamine 5.0 mL (ca. 6 equivalents) at 150° C. for 24 hours attaching with a reflux cooler and during which time added more 3-methylbutylamine 2.5 mL. Removed was the excess amine under the reduced pressure and allowed to cool to room temperature to give a colorless solid. Purification by recrystallization from ethyl ether gave N,N'-bis(3-methylbutyl)urea 1.29 g as white plates (64.5% yield).

NMR (CDCl$_3$) δ0.91 (6H, d, J=6.9 Hz), 1.38 (2H, q, J=7.2 Hz), 1.63 (1H, m), 3.15 (2H, t, J=7.3 Hz).

REFERENTIAL EXAMPLE 3

Preparation of 1,3-Dibenzylbarbituric Acid

Heated was a mixture of N,N'-dibenzylurea 12.02 g (50.0 mmol) and malonic acid 5.20 g (50.0 mmol) in acetic anhydride 50.0 mL (530 mmol, 10.6 equivalents) at 70° C.–75° C. for 14 hours under a nitrogen atmosphere. Then, removed were the volatile materials under the reduced pressure and distributed the residue between layers of 2 M sodium hydroxide 250 mL and ether 200 mL. Separated was the alkaline aqueous layer and after washing with ether, neutralized with concentrated hydrochloric acid under cooling in ice-water bath (pH 2–3). Extracted was the neutralized aqueous solution with chloroform, washed with water, and dried over sodium sulfate. Removal of the solvent under reduced pressure gave 1,3-dibenzylbarbituric acid 14.7 g as pale yellow crystalline powder (95.6% yield).

NMR (CDCl$_3$) δ3.60 (1H, s), 5.00 (2H, s), 7.22–7.45 (5H, m).

REFERENTIAL EXAMPLE 4

Preparation of 1,3-Bis(3-methylbutyl)barbituric Acid

Heated was a mixture of N,N'-bis(3-methylbutyl)urea 1.28 g (6.39 mmol) and malonic acid 665 mg (6.39 mmol) in acetic anhydride 6.4 mL (68 mmol, 11 equivalents) at 70° C.–75° C. under a nitrogen atmosphere for 4 hours. Removed were the volatile materials under the reduced pressure and distributed the residue between layers of 2 M sodium hydroxide 50 mL and ether 60 mL. Separated was the alkaline aqueous layer and after washing with ether, neutralized aqueous solution with concentrated hydrochloric acid (pH 2–3). Extracted was the neutrallized aqueous solution with dichloromethane, washed with water, and dried over sodium sulfate. Removal of the solvent under the reduced pressure gave orange solid 1.22 g. Purified was the crude product by column chromatography (silica gel, ether elution) to obtain 1,3-bis(3-methylbutyl)barbituric acid 954 mg as pale yellow crystals (95.6% yield).

NMR (CDCl$_3$) δ0.95 (6H, d, J=6.6 Hz), 1.48 (2H, q, J=7.8 Hz), 1.62 (1H, m), 3.65 (1H, s), 3.87 (2H, t, J=7.8 Hz).

EXAMPLE 1

Synthesis of 1,3-Dibenzyl-5-(3-methyl-1-oxobutyl) barbituric Acid (Compound No. 1)

To a solution of 1,3-dibenzyl barbituric acid 265 mg (0.859 mmol) in dry dichloromethane 2.0 mL under a nitrogen atmosphere, added was pyridine 1.0 mL (12 mmol) and stirred at 0° C. Added was isovaleryl chloride 104 mg (0.858 mmol, 1.00 equivalent) in dichloromethane 1.0 mL to the solution slowly during a period of 20 minutes, then stirred at room temperature for 3 hours. Added was dichloromethane 50 mL and washed the organic layer with 2 M hydrochloric acid and saturated brine, and dried over sodium sulfate. Purified was the crude product 351 mg, after removal of the solvent under the reduced pressure, by column chromatography (silica gel, eluted with dichloromethane). It obtained 1,3-dibenzyl-5-(3-methyl-1-oxobutyl)barbituric acid 299 mg as colorless viscous oil at first, and in 2 days it turned white plates (88.7% yield).

NMR (CDCl$_3$) δ1.01 (6H, d, J=6.6 Hz), 2.20 (1H, m), 3.04 (2H, d, J=6.8 Hz), 5.10 (2H, s), 5.11 (2H, s), 7.23–7.47 (10H, m).

EXAMPLE 2

Synthesis of 1,3-Dibenzyl-5-(phenylacetyl) barbituric Acid (Compound No. 2)

To a solution of 1,3-dibenzyl barbituric acid 192 mg (0.623 mmol) in dry dichloromethane 2.0 mL under nitrogen atmosphere, added was pyridine 1.0 mL (12 mmol) and stirred at 0° C. Added was phenylacetyl chloride 96 mg (0.623 mmol, 1.00 equivalent) in dichloromethane 1.0 mL to the solution slowly during a period of 20 minutes, then stirred at room temperature for 3 hours. Added was dichloromethane 40 mL and washed the organic layer with 2 M hydrochloric acid and saturated brine, and dried over sodium sulfate. Purified was the crude product 273 mg, after removal of the solvent under the reduced pressure, by column chromatography (silica gel, eluted with dichloromethane). It obtained 1,3-dibenzyl-5-(phenylacetyl) barbituric acid 236 mg as colorless viscous oil at first (88.7% yield) and it gradually turned white plates.

NMR (CDCl$_3$) δ4.51 (2H, s), 5.09 (2H, s), 5.12 (2H, s), 7.25–7.60 (15H, m).

EXAMPLE 3

Synthesis of 1,3-Dibenzyl-5-(2-thienylacetyl) barbituric Acid (Compound No. 3)

To a solution of 1,3-dibenzylbarbituric acid 154 mg (0.500 mmol) in dry dichloromethane 2.0 mL under a nitrogen atmosphere, added was pyridine 1.0 mL (12 mmol) and stirred at 0° C. Added was 2-thienylacetyl chloride 80 mg (0.50 mmol, 1.00 equivalent) in dichloromethane 1.0 mL to the solution slowly during a period of 20 minutes, then stirred at room temperature for 3 hours. Added was ether 50 mL and washed the organic layer with 2 M hydrochloric acid and saturated brine, and dried over sodium sulfate. Purified was the crude product 216 mg after removal of the solvent under the reduced pressure, by column chromatography (silica gel, eluted with dichloromethane). It obtained 1,3-dibenzyl-5-(2-thienylacetyl)barbituric acid 153 mg as yellow viscous oil (56.9% yield).

NMR (CDCl$_3$) δ4.68 (2H, s), 5.09 (2H, s), 5.13 (2H, s), 6.94 (1H, dd, J=3.5, 5.3 Hz), 7.03 (1H, dd, J=1.1, 3.5 Hz), 7.20 (1H, dd, J=1.1, 5.3 Hz), 7.23–7.50 (10H, m).

EXAMPLE 4

Synthesis of 1,3-Bis(3-methylbutyl)-5-(3-methyl-1-oxobutyl)barbituric Acid (Compound No. 4)

To a solution of 1,3-bis(3-methylbutyl)barbituric acid 268 mg (1.00 mmol) in dry dichloromethane 3.0 mL under a nitrogen atmosphere, added was pyridine 0.81 mL (0.79 g, 10 mmol, 10 equivalents) and stirred at 0° C. Added was isovaleryl chloride 121 mg (1.00 mmol, 1.00 equivalent) in dichloromethane 1.5 mL to the solution slowly during a period of 20 minutes, then stirred at room temperature for 4 hours. Added was dichloromethane 40 mL and washed the organic layer with 2 M hydrochloric acid and saturated brine, and dried over sodium sulfate. Purified was the crude product 383 mg, after removal of the solvent under the reduced pressure, by column chromatography (silica gel, eluted with dichloromethane). It obtained 1,3-bis(3-methylbutyl)-5-(3-methyl-1-oxobutyl)barbituric acid 278 mg as white plates (79.0% yield).

NMR (CDCl$_3$) δ0.97 (6H, d, J=6.6 Hz), 1.02 (12H, d, J=6.6 Hz), 1.52 (2H, m), 1.64 (2H, m), 2.20 (1H, m), 3.04 (2H, d, J=7.1 Hz), 3.91 (4H, m).

Test 1

(1) Preparation of cells

ICR mice 11–12 days old (Charles River) were subjected to euthanasia through ether anesthesia, and disinfected by dipping in 70% ethanol immediately. Subsequently, a femur and a shank of a mouse was removed, chopped in an -MEM culture medium (Flow Labs Corp.) containing 5% FBS (Irving Scientific Corp.), 100 U/mL penicillin, and 100 g/mL streptomycin. Supernatant obtained by pipetting was collected, washed with culture medium solution, suspended in a solution containing 5% FBS and -MEM culture medium to yield osteocytes containing osteoclasts. Supernatant of osteocyte suspending solution was taken 3 minutes after standing still to pass through meshes (Cell Strainer, 70 m, Falcon Corp.). The filtrate was adjusted to the concentration of 1 10$^7$ cells/mL to use for pit formation assay.

(2) Test by the pit formation assay

An ivory piece was cut into slices in 150 m thickness by using a precision, low speed cutter (Buehler Corp.) and punched to make a cylinderial holes in 6 mm diameter. The ivory piece was dipped in 70% ethanol, treated by sonication for 5 minutes twice, and washed with sterilized PBS three times and with culture medium twice. The ivory piece was put in pits of a 96-pit culture plate (Falcon Corp.), 100 μl of culture medium, that contains a chemical compound of the present invention adjusted to a concentration of 2×10$^{-5}$ M, was poured into each pit, and 100 μL of culture medium, that contains 1×10$^7$ osteocytes/mL previously prepared, into each pit (the final concentration of the compound was 1×10$^{-5}$ M), and finally cultivation was carried out in an incubator under 37° C. and 10% CO$_2$ for 3 days. Then cells on an ivory piece were removed in 2 M sodium hydroxide solution, washed with water and methanol to stain resorption cavity with Coomassie Brilliant Blue and count numbers of absorbed cavities under a microscope. The inhibition rate of bone resorption was calculated on the basis that resorption cavity was assumed 0% in the case of no addition of the compound under the presence of rPTH ($1\times10^{-8}$ M) in the solution and the case of no resorption cavity was assumed 100%. A good result was yielded in the same experiment with variation of resorption cavity numbers among experimental groups due to a difference among proportions of various cell in the solution, in which osteocytes were suspended, and also among the lot numbers of used animals.

Table 1 shows a result. As clearly shown by the result, the compound of the present invention shows a distinct inhibiting rate of bone resorption and is useful as a substance having an action to inhibit bone resorption.

TABLE 1

| Added Compound No. | Concentration of Compound (M) | Number of resorption cavity (mean ± SD) | Number of resorption cavity at no addition of Compound (mean ± SD) | Inhibiting rate (%) |
|---|---|---|---|---|
| 1 | $1 \times 10^{-5}$ | 1.0 ± 0.5 | 224.0 ± 20.0 | 99.2 |
| 2 | $1 \times 10^{-5}$ | 2.2 ± 0.6 | 224.0 ± 20.0 | 99.0 |
| 3 | $1 \times 10^{-5}$ | 7.0 ± 1.7 | 179.6 ± 34.4 | 96.7 |
| 4 | $1 \times 10^{-5}$ | 21.1 ± 4.3 | 224.0 ± 20.0 | 90.6 |

What is claimed is:

1. A method of treating diseases of bones and cartilage in warm-blooded animals comprising administering to warm-blooded animals an amount of a compound selected from the group consisting of a compound of the formula

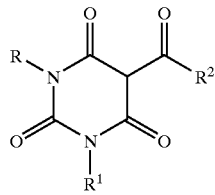

I wherein R and $R^1$ are individually selected from the group consisting of unsubstituted or substituted alkyl and alkenyl of 3 to 15 carbon atoms and unsubstituted or substituted arylmethyl, $R^2$ is 2-thienylmethyl and unsubstituted or substituted arylmethyl, the substituents being at least one member of the group consisting of —OH, —NH$_2$, alkoxy of up to 10 carbon atoms, alkylthio of up to 10 carbon atoms, mono- and dialkylamino, halogen, —CN, —NO$_2$, alkylenedioxy, alkyl of up to 10 carbon atoms and aryl and its pharmaceutical salts sufficient to treat bone and cartilage disease.

2. The method of claim 1 wherein $R^1$ is 2-thienylmethyl.

3. The method of claim 1 wherein the active compound is selected from the group consisting of 1,3-dibenzyl-5-(3-methyl-1-oxobutyl)barbituric acid, 1,3-dibenzyl-5-(phenylacetyl)barbituric acid, 1,3-dibenzyl-5-(2-thienylacetyl)barbituric acid and 1,3-bis(3-methylbutyl)-5-(3-methyl-1-oxobutyl)barbituric acid.

4. The method of claim 1 wherein the compound selected from the group consisting of
1,3-dibenzyl-5-(3-methyl-1-oxobutyl)barbituric acid,
1,3-dibenzyl-5-(phenylacetyl)barbituric acid,
1,3-dibenzyl-5-(3-thienylacetyl)barbituric acid,
1-benzyl-3-(3-methylbutyl)-5-(3-methyl-1-oxobutyl)barbituric-acid,
1-benzyl-3-(3-methylbutyl)-5-(phenylacetyl)barbituric acid,
1-benzyl-3-(3-methylbutyl)-5-(2-thienylacetyl)barbituric-acid,
1-benzyl-3-(3-methyl-2-butenyl)-5-(3-methyl-1-oxobutyl)barbituric acid,
1-benzyl-3-(3-methyl-2-butenyl)-5-(phenylacetyl)barbituric acid, and
1-benzyl-3-(3-methyl-2-butenyl)-5-(2-thienylacetyl)barbituric acid.

5. A composition for treating bone and cartilage diseases comprising an amount of a compound selected from the group consisting of a compound of the formula

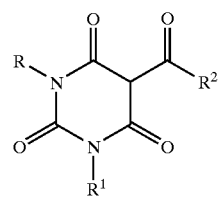

I wherein R and $R^1$ are individually selected from the group consisting of unsubstituted or substituted alkyl and alkenyl of 3 to 15 carbon atoms and unsubstituted or substituted arylmethyl, $R^2$ is 2-thienylmethyl and unsubstituted or substituted arylmethyl, the substituents being at least one member of the group consisting of —OH, —NH$_2$, alkoxy of up to 10 carbon atoms, alkylthio of up to 10 carbon atoms, mono- and dialkylamino, halogen, —CN, —NO$_2$, alkylenedioxy, alkyl of up to 10 carbon atoms and aryl and its pharmaceutical salts sufficient to treat bone and cartilage disease and an inert pharmaceutical carrier.

* * * * *